United States Patent
Kadota et al.

(10) Patent No.: US 6,992,200 B2
(45) Date of Patent: Jan. 31, 2006

(54) COPPER COMPLEXES AND PROCESS FOR FORMATION OF COPPER-CONTAINING THIN FILMS BY USING THE SAME

(75) Inventors: Takumi Kadota, Yamaguchi (JP); Chihiro Hasegawa, Yamaguchi (JP); Kouhei Watanuki, Yamaguchi (JP)

(73) Assignee: UBE Industries, Ltd., (JP)

( * ) Notice: Subject to any disclaimer, the term of this patent is extended or adjusted under 35 U.S.C. 154(b) by 8 days.

(21) Appl. No.: 10/503,064

(22) PCT Filed: Jan. 31, 2003

(86) PCT No.: PCT/JP03/01014

§ 371 (c)(1),
(2), (4) Date: Jul. 30, 2004

(87) PCT Pub. No.: WO03/064437

PCT Pub. Date: Aug. 7, 2003

(65) Prior Publication Data

US 2005/0080282 A1    Apr. 14, 2005

(30) Foreign Application Priority Data

Jan. 31, 2002 (JP) .............. 2002-022798
Sep. 6, 2002 (JP) .............. 2002-261357

(51) Int. Cl.
  *C07F 1/08*    (2006.01)
  *C23C 16/00*   (2006.01)
(52) U.S. Cl. .............. 556/10; 556/12; 556/40; 556/117; 427/248.1; 427/587; 438/687
(58) Field of Classification Search ............ 556/10, 556/12, 40, 117; 427/248.1, 587; 438/687
See application file for complete search history.

(56) References Cited

U.S. PATENT DOCUMENTS 6,090,960 A * 7/2000 Senzaki et al. .............. 556/9
6,372,928 B1 * 4/2002 Kawaguchi et al. .......... 556/10
6,642,401 B2 * 11/2003 Watanabe et al. ............ 556/12
6,838,573 B1 * 1/2005 Farnia et al. ................ 556/41

* cited by examiner

*Primary Examiner*—Porfirio Nazario-Gonzalez
(74) *Attorney, Agent, or Firm*—Nixon Peabody LLP; Jeffrey L. Costellia

(57) ABSTRACT

Copper-containing thin films can be industrially advantageously formed by chemical vapor deposition using as the copper source a divalent copper complex bearing β-diketonato ligands having silyl ether linkage. A representative example of the divalent copper complex is represented by the formula (I):

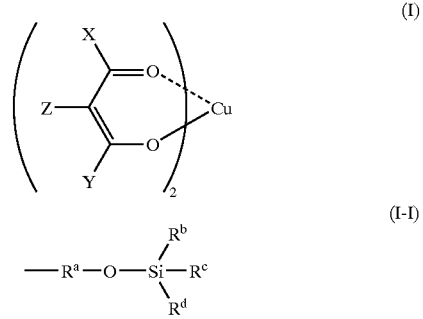

wherein Z is hydrogen or alkyl; X is a group represented by the formula (I—I), in which $R^a$ is alkylene, and each of $R^b$, $R^c$ and $R^d$ is alkyl; and Y is an alkyl group or a group represented by the formula (I—I), in which $R^a$ is alkylene, and each of $R^b$, $R^c$ and $R^d$ is alkyl.

14 Claims, 1 Drawing Sheet

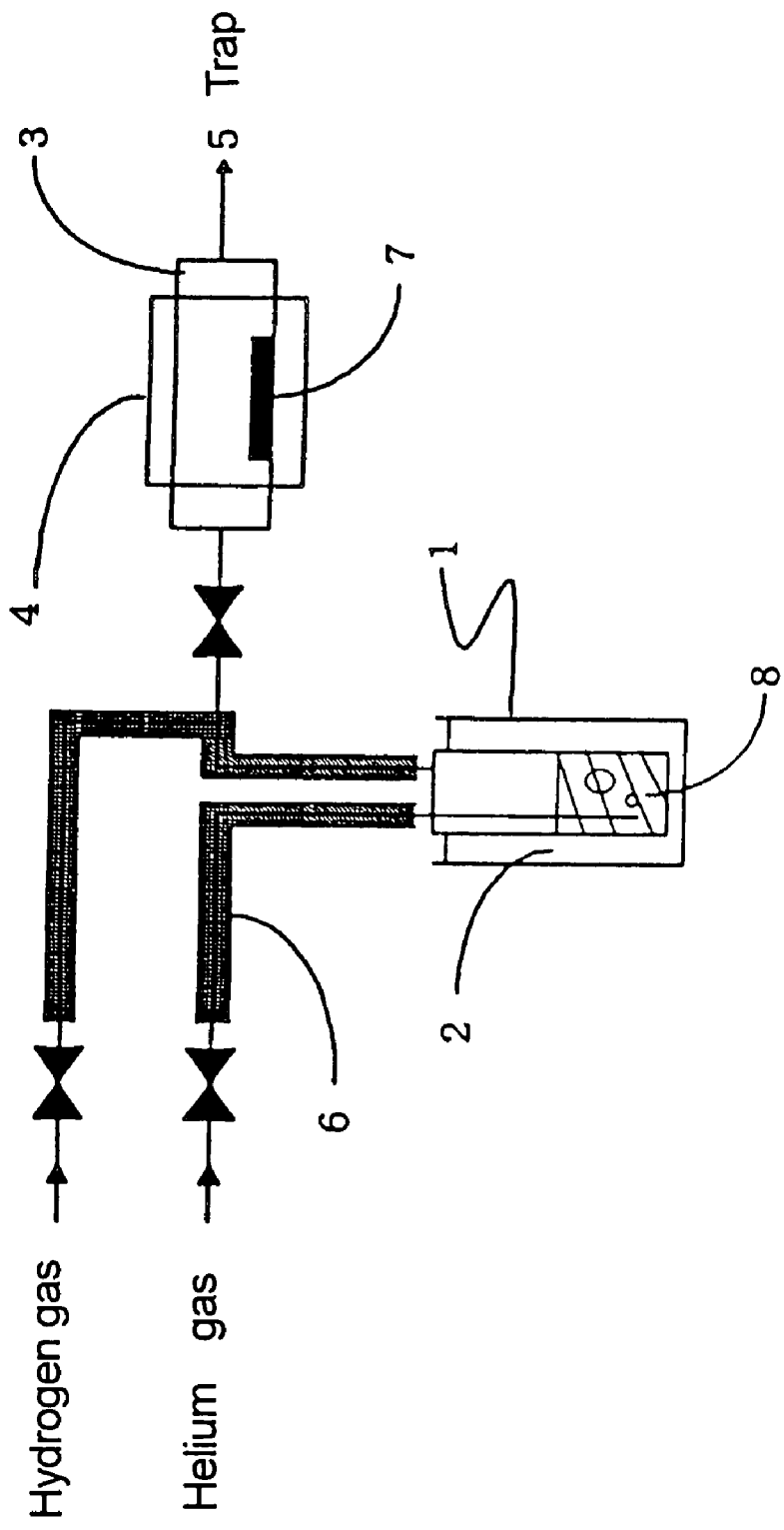
FIGURE

COPPER COMPLEXES AND PROCESS FOR FORMATION OF COPPER-CONTAINING THIN FILMS BY USING THE SAME

FIELD OF INVENTION

The present invention relates to a copper complex which is advantageously employable for producing a thin metal film comprising copper or copper alloy or a thin metal film comprising a complex metal oxide containing copper by chemical vapor deposition. The invention further relates to a process for producing a thin metal film comprising copper or copper alloy or a thin metal film comprising a complex metal oxide containing copper from the above-mentioned copper complex.

BACKGROUND OF INVENTION

A metallic copper thin film (hereinafter simply referred to as "copper thin film") is employable as a copper circuit of a silicon semiconductor. A metal oxide thin film containing copper oxide (hereinafter simply referred to as "copper oxide thin film") is expected as material for high-critical temperature superconductors.

As the processes for producing the copper thin film or complex oxide thin film containing copper oxide by vapor deposition procedure, various processes are known. A representative process is a chemical vapor deposition process (CVD process) comprising the steps of thermally decomposing a compound containing a copper atom under specific conditions and depositing the decomposition product on a substrate to produce thereon a copper thin film or a copper oxide thin film.

For the production of a copper thin film or a copper oxide thin film in the CVD process, β-diketonato copper complexes are generally used.

JP-A-5-59551 describes a process for producing a copper thin film (to be used as a copper circuit of a silicon semiconductor) using a β-diketonato copper(I) as a copper source. The β-diketonato copper(I) is advantageously employed because it can be subjected to disproportionation reaction, to deposit metallic copper. However, it has such a defect that the β-diketonato copper (I) is thermally unstable, and that some of β-diketonato copper(I) decompose when these are heated to vaporize in the CVD process.

A typical divalent β-diketonato copper complex employed in the CVD process is dipivaloylmethanato copper(II) complex. This copper complex is more thermally stable than the monovalent β-diketonato copper complex. However, since the dipivaloylmethanato copper(II) complex has such a high melting point as 198° C., it likely deposits in a CVD system and plugs the production line. Other known β-diketonato copper complexes also have the same problem. Moreover, since the dipivaloylmethanato copper (II) complex and other known β-diketonato copper complexes have a low vapor pressure, the thin film production rate is low. Accordingly, these known β-diketonato copper complexes are not appropriate as industrially employable copper sources.

JP-A-2001-181840 describes a β-diketonato copper(II) complex having the following formula (II):

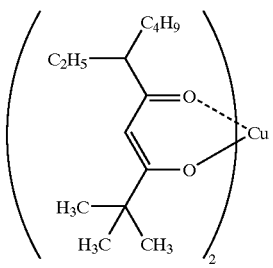

which is liquid at room temperature and solves the problems of the known material.

The above-mentioned β-diketonato copper(II) complex exists as a viscous liquid at temperature. Therefore, it is easily supplied in the CVD system and free from the problem of plugging. Nevertheless, it still shows a low film production rate, and therefore, some of the problems in the production workability are still unsolved.

DISCLOSURE OF INVENTION

It is an object of the present invention to provide a copper complex which has a low melting point and is thermally stable, so that it is favorably employable as the copper source in the CVD process for producing a copper thin film or a copper oxide thin film.

It is another object of the invention to provide a process for producing a copper-containing thin film such as a copper thin film or a copper oxide thin film in which the above-mentioned copper complex is used.

The present inventors have discovered that a copper complex having β-diketonato ligands containing a silyl ether linkage can solve the above-mentioned problems. The present inventors have been complete based on this discovery.

Accordingly, the present invention resides in a divalent copper complex having β-diketonato ligands containing a silyl ether linkage.

The invention also resides in a method of forming a copper-containing film by chemical vapor deposition using a copper(II) complex having β-diketonato ligands containing a silyl ether linkage as a copper source.

As the β-diketonato ligands containing a silyl ether linkage, a compound represented by the formula (I)' is preferred:

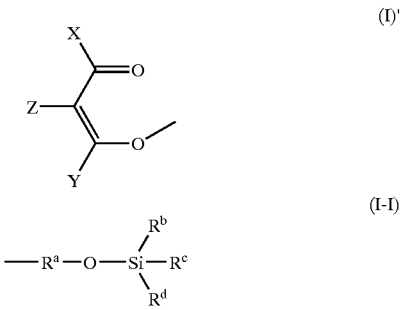

in which Z is a hydrogen atom or an alkyl group having 1–4 carbon atoms; X is a group represented by the formula (I—I), in which $R^a$ is a linear or branched alkylene group having 1–5 carbon atoms, and each of $R^b$, $R^c$ and $R^d$ independently is a linear or branched alkyl group having 1–5 carbon atoms; and Y is a linear or branched alkyl group having 1–8 carbon atoms or a group represented by the formula (I—I), in which $R^a$ is a linear or branched alkylene group having 1–5 carbon atoms, and each of $R^b$, $R^c$ and $R^d$ independently is a linear or branched alkyl group having 1–5 carbon atoms.

As the copper complex of the invention, a compound represented by the formula (I) is preferred:

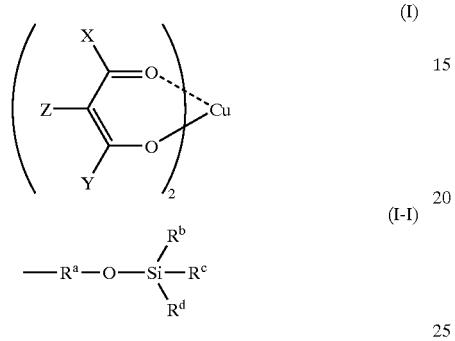

(I)

(I-I)

in which Z is a hydrogen atom or an alkyl group having 1–4 carbon atoms; X is a group represented by the formula (I—I), in which $R^a$ is a linear or branched alkylene group having 1–5 carbon atoms, and each of $R^b$, $R^c$ and $R^d$ independently is a linear or branched alkyl group having 1–5 carbon atoms; and Y is a linear or branched alkyl group having 1–8 carbon atoms or a group represented by the formula (I—I), in which $R^a$ is a linear or branched alkylene group having 1–5 carbon atoms, and each of $R^b$, $R^c$ and $R^d$ independently is a linear or branched alkyl group having 1–5 carbon atoms.

In the formulas, it is preferred that X is the same as Y. Y preferably is a linear or branched alkyl group having 1–8 carbon atoms. $R^a$ preferably is an alkylene group of 1–3 carbon atoms which may carry one or more alkyl substituents. Particularly preferred is that Z is hydrogen and each of $R^b$, $R^c$ and $R^d$ is methyl.

BRIEF DESCRIPTION OF DRAWING

FIG. 1 is a schematic view of a CVD system which can be employed for the copper thin film production, wherein 1 denotes a glass ampul, 2 denotes a heater (vaporizer), 3 denotes a reactor, 4 denotes a heater (reactor), 5 denotes a trap, 6 denotes a heater (for pre-heating), 7 denotes a substrate, and 8 denotes a copper complex source.

DETAILED DESCRIPTION OF INVENTION

In the invention, examples of the β-diketonato ligands containing a silyl ether linkage include the compounds of the following formulas (III)' to (XIV)':

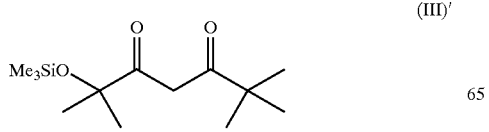

(III)'

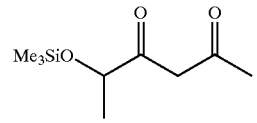

(IV)'

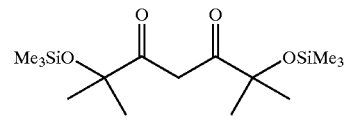

(V)'

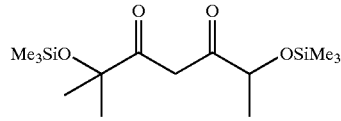

(VI)'

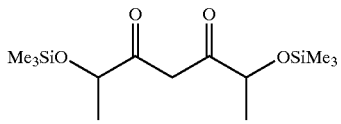

(VII)'

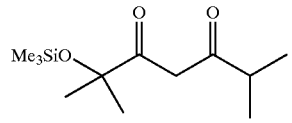

(VIII)'

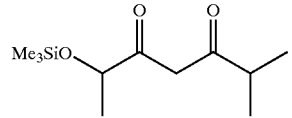

(IX)'

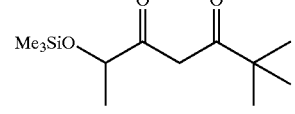

(X)'

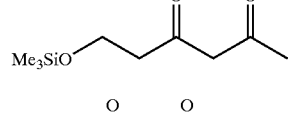

(XI)'

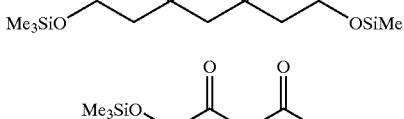

(XII)'

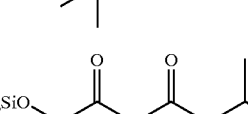

(XIII)'

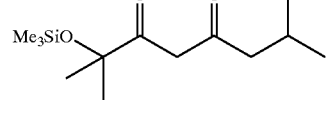

(XIV)'

The above-illustrated β-diketone compounds can be obtained according to the below-illustrated scheme, in which a silylated ketone is reacted with a silylated organic acid ester in the presence of a base, or a silylated organic acid ester is reacted with a ketone in the presence of a base, and the reaction product is treated with an acid. The acid-treated product was purified by distillation or column chromatography. Other known processes also are utilizable.

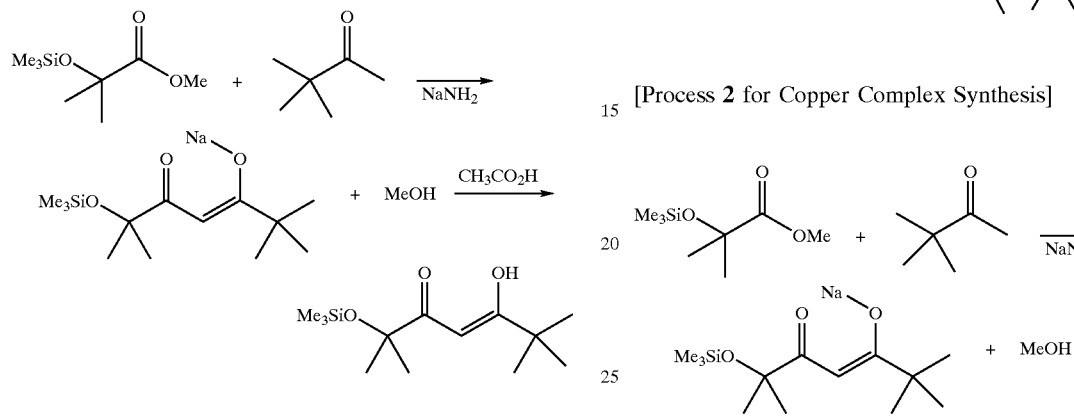

The β-ketonato copper complex, i.e., a copper complex in which an enolate anion of β-diketone is coordinated to copper, can be obtained by a reaction between β-diketone and copper hydroxide (below-illustrated process 1 for copper complex synthesis) or a reaction between an enolate anion of β-diketone and a copper salt such as cupric chloride (below-illustrated process 2 for copper complex synthesis). The synthesis can be performed in most organic solvents such as hydrocarbons (e.g., hexane and toluene), ethers (e.g., tetrahydrofuran (THF) and dimethoxyethane), nitrites (e.g., acetonitrile), halogenated hydrocarbons (e.g., dichloromethane), alcohols (e.g., isopropanol), and esters (e.g., ethyl acetate). Water produced in the process 1 can be distilled off together the solvent (e.g., toluene) by azeotropic distillation. When such a solvent as THF is used, water is removed from the reaction mixture by distillation under reduced pressure at room temperature together with the solvent. Otherwise, water can be removed using a dehydrating agent such as anhydrous sodium sulfate, anhydrous magnesium sulfate, anhydrous copper sulfate, molecular sieves, or nonionic water-absorbing polymer.

[Process 1 for Copper Complex Synthesis]

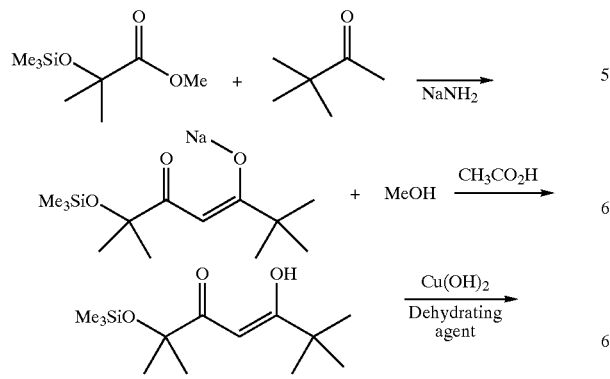

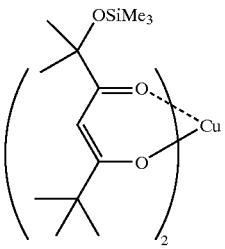

[Process 2 for Copper Complex Synthesis]

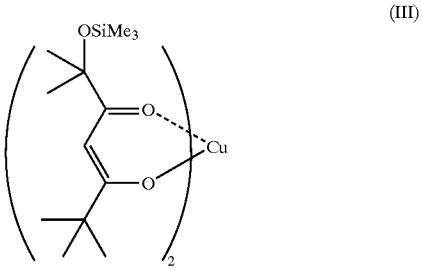

The produced copper complex can be purified by column chromatography using commercially available silica gel for chromatography or a dehydrated silica gel which is prepared by dehydrating the commercially available silica gel, or by distillation, or by their combination.

An example of the copper complex having the silylether type β-diketonato ligand is represented by the following formula (III):

(III)

The copper complex of the formula (III) is a copper complex having a β-diketone enolate anion ligand of the aforementioned formula (III)' which corresponds a compound of the aforementioned formula (I) in which X is $(CH_3)_3SiO—C(CH_3)_2—$, Y is $(CH_3)_3C—$, and Z is H, namely, bis-(2,6,6-trimethyl-2-(trimethylsilyloxy)-3,5-heptadionato) copper(II) complex [hereinafter referred to as $Cu(sobd)_2$].

The β-diketones of the aforementioned formulas (IV)' to (XIV)' give the below-illustrated copper complexes (IV) to (XIV), respectively, which have an enolate anion of the corresponding β-diketone.
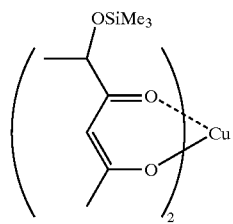
(IV)
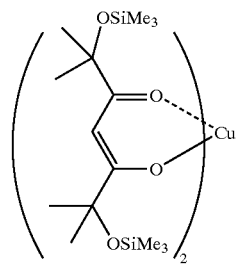
(V)
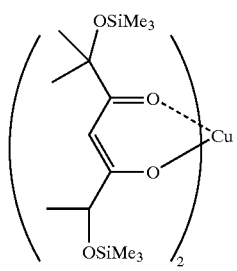
(VI)
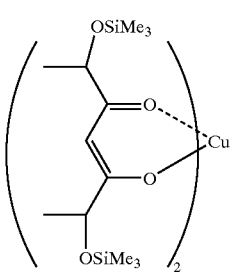
(VII)
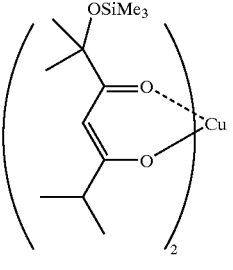
(VIII)
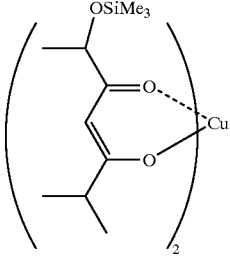
(IX)
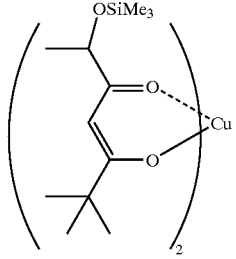
(X)
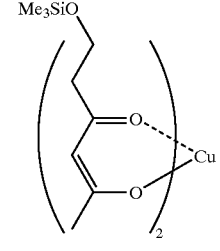
(XI)
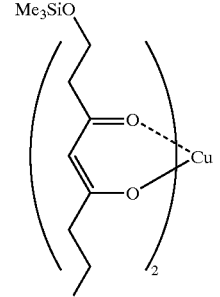
(XII)
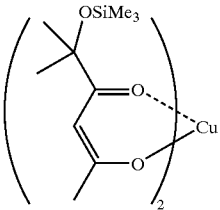
(XIII)

-continued

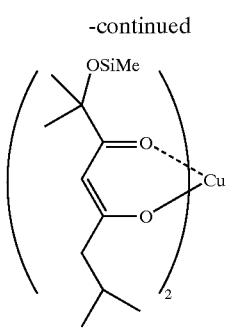

(XIV)

The copper complex of the invention can be employed for producing a copper-containing thin film by chemical vapor deposition in the known CVD system as illustrated in FIG. 1.

The vaporization of the copper complex in the chemical vapor deposition process can be performed by directly supplying the copper complex into a vaporization chamber, or by diluting the copper complex with an appropriate solvent (e.g., hexane, toluene, or tetrahydrofuran) and supplying thus produced solution into a vaporization chamber.

The deposition on a substrate can be performed by the known CVD process. The copper complex is thermally decomposed under reduced pressure or in the presence of an inert gas. Otherwise, the copper complex can be decomposed and deposited in the presence of a reducing gas such as hydrogen gas. Also employable is a plasma CVD process using a hydrogen gas to deposit metallic copper. Further, thermal decomposition or plasma CVD of the copper complex in the presence of oxygen can be also employed for deposition of a copper oxide thin film.

The invention is further illustrated by the following examples.

EXAMPLE 1

(1) Synthesis of 2,6-dimethyl-2,6-di(trimethylsilyloxy)-3,5-heptadione [Represented by the Formula (V)', hereinafter Referred to as "dsobd"]

In a 50 mL-volume flask were placed 1.80 g (45.0 mmol) of 60% sodium hydride and 9.83 g (51.7 mmol) of methyl 2-(trimethylsilyloxy)-2-methyl-propionate. The resulting solution was heated to 120° C., and to the heated solution was dropwise added slowly a solution of 3.00 g (17.2 mmol) of 2-(trimethylsilyloxy)-2-methyl-3-butanone in 9 mL of toluene. After the dropwise addition was complete, the reaction mixture was heated at 120° C. for one hour. Subsequently, the reaction mixture was cooled to room temperature and made weak acidic by the addition of an acetic acid-toluene mixture. The precipitated sodium acetate was removed by filtration, to obtain a yellow solution.

The obtained solution was concentrated and purified by column chromatography using dehydrated silica gel, to give 1.20 g (3.61 mmol, yield 21%) of the desired main product, i.e., 2,6-dimethyl-2,6-di(trimethylsilyloxy)-3,5-heptadione.

The product was identified by NMR, IR, and MS.

$^1$H-NMR (CDCl$_3$): δ 0.15 (s, 9H), 1.41 (s, 9H), 4.00 (s, 0.4H), 6.43 (s, 0.8H), 15.55 (s, 0.8H) IR (cm$^{-1}$): 2961, 1605(br), 1252, 1198, 1048, 842 MS (m/e): 332

(2) Preparation of Cu(dsobd)$_2$ [bis(2,6-dimethyl-2,6-di(trimethylsilyloxy)-3,5-heptadionato) copper(II) Complex]

Since production of the desired β-diketone was confirmed in the above-mentioned procedure, the desired copper complex was prepared by adding a copper source to a product prepared in the same manner.

In a 50 mL-volume flask were placed 1.80 g (45.0 mmol) of 60% sodium hydride and 9.83 g (51.7 mmol) of methyl 2-(trimethylsilyloxy)-2-methyl-propionate. The resulting solution was heated to 120° C., and to the heated solution was dropwise added slowly a solution of 3.00 g (17.2 mmol) of 2-(trimethylsilyloxy)-2-methyl-3-butanone in 9 mL of toluene. After the dropwise addition was complete, the reaction mixture was heated at 120° C. for one hour. Subsequently, the reaction mixture was cooled to 30° C. There was produced 1.28 g (3.61 g) of 2,6-dimethyl-2,6-di(trimethylsilyloxy)-3,5-heptadionato sodium salt. To the reaction solution was added 0.24 g (1.78 mmol) of cupric chloride. The reaction solution was immediately turned to dark green. The solution was continuously stirred at 80° C. for 2 hours and cooled to room temperature. Then, the reaction solution was washed with water. The obtained organic portion was dried, and purified by column chromatography using dehydrated silica gel, to give 1.10 g (1.52 mmol, yield 85%, based on the amount of cupric chloride) of bis(2,6-dimethyl-2,6-di(trimethylsilyloxy)-3,5-heptadionato) copper(II) complex.

The product was identified by IR and elemental analysis.

IR (cm$^{-1}$): 2978, 1567, 1498, 1414, 1252, 1197, 1045, 842 Elemental analysis for C$_{30}$H$_{62}$O$_8$Si$_4$Cu Found: C, 49.0%; H, 8.99%; Cu, 8.6%. Calculated: C, 49.6%; H, 8.60%; Cu, 8.74%.

In the IR spectrum, a peak of 1,605 cm$^{-1}$ assignable to β-diketone disappeared, and a peak of 1,567 cm$^{-1}$ assignable to diketonato was observed. Accordingly, it was confirmed that the desired copper complex was produced. This copper complex is a new compound.

EXAMPLE 2

(1) Synthesis of 2,6,6-trimethyl-2-(trimethylsilyloxy)-3,5-heptadione [Represented by the Formula (III)', hereinafter Referred to as "sobd"]

In a 50 mL-volume flask, 0.40 g (10.3 mmol) of sodium amide and 1.20 g (12.0 mmol) of pinacolin were suspended in 3 mL of toluene, and the resulting suspension was stirred for 30 min. at room temperature. Subsequently, a solution of 1.00 g (5.25 mmol) of methyl 2-(trimethylsilyloxy)-2-methyl-propionate in 6 mL of toluene was dropwise added slowly. After the dropwise addition was complete, the mixture was subjected to reaction for one hour at room temperature. The reaction mixture was then made weak acidic with an acetic acid-toluene mixture. The precipitated sodium acetate was removed by filtration to give a yellow solution.

The obtained solution was concentrated and purified by column chromatography using dehydrated silica gel, to give 0.83 g (3.21 mmol, yield 61%) of the desired main product, i.e., 2,6,6-trimethyl-2-(trimethylsilyloxy)-3,5-heptadione.

The product was identified by NMR, IR, and MS.

$^1$H-NMR (CDCl$_3$): δ 0.14 (s, 9H), 1.17 (s, 9H), 1.39 (s, 6H), 3.86 (s, 0.3H), 6.09 (s, 0.85H), 15.72 (s, 0.85H) IR (cm$^{-1}$) 2966, 1600(br), 1252, 1197, 1045, 841 MS (m/e) 258

(2) Preparation of Cu(sobd)$_2$ [bis(2,6,6-trimethyl-2-(trimethylsilyloxy)-3,5-heptadionato) copper(II) Complex, Represented by the Formula (III)]

Since production of the desired β-diketone was confirmed in the above-mentioned procedure, the desired copper complex was prepared by adding a copper source to a product prepared in the same manner.

In a 50 mL-volume flask, 0.40 g (10.3 mmol) of sodium amide and 1.20 g (12.0 mmol) of pinacolin were suspended in 3 mL of toluene, and the resulting suspension was stirred for 30 min. at room temperature. Subsequently, a solution of 1.00 g (5.25 mmol) of methyl 2-(trimethylsilyloxy)-2-methyl-propionate in 6 mL of toluene was dropwise added slowly. After the dropwise addition was complete, the mixture was subjected to reaction for one hour at room temperature. To the reaction solution was added 0.22 g (1.60 mmol) of cupric chloride. The reaction solution immediately turned to dark green. The solution was continuously stirred for one hour at room temperature. Then, the reaction solution was washed with water. The obtained organic portion was dried, and purified by column chromatography using dehydrated silica gel, to give 0.80 g (1.38 mmol, yield 86%, based on the amount of cupric chloride) of bis(2,6,6-trimethyl-2-(trimethylsilyloxy)-3,5-heptadionato) copper(II) complex.

The product was identified by IR and elemental analysis.
IR (cm$^{-1}$) 2960, 1561, 1501, 1412, 1252, 1196, 1047, 840 Elemental analysis for $C_{26}H_{50}O_6Si_2Cu$ Found: C, 54.8%; H, 8.20%; Cu, 11%. Calculated: C, 54.0%; H, 8.71%; Cu, 11.0%.

In the IR spectrum, a peak of 1,600 cm$^{-1}$ assignable to β-diketone disappeared, and a peak of 1,561 cm$^{-1}$ assignable to diketonato was observed. This copper complex is a new compound.

EXAMPLE 3

(1) Synthesis of 2,6-dimethyl-2-(trimethylsilyloxy)-3,5-heptadione [Represented by the Formula (VIII)', hereinafter Referred to as "sopd"]

In a 50 ml-volume flask, 0.50 g (12.8 mmol) of sodium amide and 0.45 g (5.22 mmol) of 3-methyl-2-butanone were suspended in 1.5 g of hexane, and the resulting suspension was stirred at 15° C. for 30 min. Subsequently, a solution of 1.20 g (6.31 mmol) of methyl 2-(trimethylsilyloxy)-2-methyl-propionate in 3 g of hexane was dropwise added slowly. After the dropwise addition was complete, the mixture was subjected to reaction at 15° C. for one hour. The reaction mixture was then made weak acidic with an acetic acid-toluene mixture. The precipitated sodium acetate was removed by filtration to give a yellow solution.

The obtained solution was concentrated and purified by column chromatography using dehydrated silica gel, to give 0.91 g (3.71 mmol, yield 71%) of the desired main product, i.e., 2,6-dimethyl-2-(trimethylsilyloxy)-3,5-heptadione.

The product was identified by NMR, IR, and MS.
$^1$H-NMR (CDCl$_3$): δ 0.14 (s, 9H), 1.14 (s, 6H), 1.39 (s, 6H), 2.44–2.50 (m, 0.85H), 2.64–2.69 (m, 0.15H), 3.77 (s, 0.3H), 5.97 (s, 0.85H), 15.51 (s, 0.85H) IR (cm$^{-1}$): 2971, 1606(br), 1253, 1199, 1045, 842 MS (m/e): 244

(2) Preparation of Cu(sopd)$_2$ [bis(2,6-dimethyl-2-(trimethylsilyloxy)-3,5-heptadionato) copper(II) Complex, Represented by the Formula (VIII)]

Since production of the desired β-diketone was confirmed in the above-mentioned procedure, the desired copper complex was prepared by adding a copper source to a product prepared in the same manner.

In a 50 mL-volume flask, 0.50 g (12.8 mmol) of sodium amide and 0.45 g (5.22 mmol) of 3-methyl-2-butanone were suspended in 1.5 g of hexane, and the resulting suspension was stirred at 15° C. for 30 min. Subsequently, a solution of 1.20 g (6.31 mmol) of methyl 2-(trimethylsilyloxy)-2-methyl-propionate in 3 g of hexane was drop-wise added slowly. After the dropwise addition was complete, the mixture was subjected to reaction at 15° C. for one hour. To the reaction solution was added 0.25 g (1.86 mmol) of cupric chloride. The reaction solution was immediately turned to dark green. The solution was continuously stirred for one hour at room temperature. Then, the reaction solution was washed with water. The obtained organic portion was dried, and purified by column chromatography using dehydrated silica gel, to give 0.86 g (1.56 mmol, yield 84%, based on the amount of cupric chloride) of bis(2,6-dimethyl-2-(trimethylsilyloxy)-3,5-heptadionato) copper(II) complex.

The product was identified by IR and elemental analysis.
IR (cm$^{-1}$): 2965, 1592, 1501, 1428, 1252, 1199, 1044, 847 Elemental analysis for $C_{24}H_{46}O_6Si_2Cu$ Found: C, 53.2%; H, 8.53%; Cu, 11%. Calculated: C, 52.4%; H, 8.42%; Cu, 11.5%.

In the IR spectrum, a peak of 1,606 cm$^{-1}$ assignable to β-diketone disappeared, and a peak of 1,592 cm$^{-1}$ assignable to diketonato was observed. This copper complex is a new compound.

EXAMPLE 4

(1) Synthesis of sopd by Different Process

In a 50 mL-volume flask, 13.7 g (0.351 mol) of sodium amide was suspended in 200 mL of hexane and then 26.7 g (0.140 mol) of methyl 2-(trimethylsilyloxy)-2-methyl-propionate was added. To the resulting solution was dropwise added 12.1 g (0.141 mol) of 3-methyl-2-butanone, and the mixture was kept at 15° C. In the development of reaction, production of gaseous ammonia was observed. The reaction was continued at 15° C. for one hour. The reaction solution was then made weak acidic with acetic acid. The obtained hexane portion was washed with water and dried over anhydrous sodium sulfate. The dried portion was distilled at 101° C./8 mmHg, to give 18.8 g (0.770 mol, yield 55%) of the desired 2,6-dimethyl-2-(trimethylsilyloxy)-3,5-heptadione.

The product was identified by NMR, IR, and MS.
$^1$H-NMR (CDCl$_3$): δ 0.14 (s, 9H), 1.14 (s, 6H), 1.39 (s, 6H), 2.44–2.50 (m, 0.85H), 2.64–2.69 (m, 0.15H), 3.77 (s, 0.3H), 5.97 (s, 0.85H), 15.51 (s, 0.85H) IR (cm$^{-1}$): 2971, 1606(br), 1253, 1199, 1045, 842 MS (m/e): 244

In the below-described (2-1) to (2-3), a copper complex of Cu(sopd)$_2$ was prepared by three different processes.

(2-1) Preparation of Cu(sopd)$_2$ by Azeotropic Toluene Distillation Dehydration In 100 mL-volume flask were placed 4.43 g (45.4 mmol) of copper hydroxide, 22.2 g (90.8 mmol) of 2,6-dimethyl-2-(trimethylsilyloxy)-3,5-heptadione, and 50 mL of toluene. The resulting mixture was heated to 130° C., and water produced by reaction was dehydrated by azeotropic toluene distillation. The amount of the produced and distilled water was confirmed by receiving and measuring it in a water receiver. The reaction was complete within approx. one hour. The obtained dark green solution was filtered and the filtrate was concentrated to give a viscous dark green solution. The solution was distilled at 179° C./0.5 Torr to give 20.2 g (36.8 mmol, yield 81%) of the desired copper complex, namely, bis-(2,6-dimethyl-2-(trimethylsilyloxy)-3,5-heptadionato) copper(II) complex.

(2—2) Preparation of Cu(sopd)$_2$ at Room Temperature in THF Solvent

The desired Cu(sopd)$_2$ can be prepared by reacting 2,6-dimethyl-2-(trimethylsilyloxy)-3,5-heptadione with copper (II) hydroxide in an organic solvent such as ether, acetonitrile, alcohol, ketone, ester, or hydrocarbon at room temperature. The following is a preparing procedure in a THF solvent.

In 100 mL-volume flask were placed 4.50 g (46.2 mmol) of copper hydroxide, 22.6 g (92.3 mmol) of 2,6-dimethyl-2-(trimethylsilyloxy)-3,5-heptadione, and 50 mL of THF. The resulting mixture was stirred for one hour at room temperature in the absence of a dehydrating agent. The resulting dark blue solution was filtered, and the THF solvent was distilled off to leave a viscous dark green solution. The solution was distilled at 179° C./0.5 Torr to give 21.1 g (38.3 mmol, yield 83%) of the desired copper complex, namely, bis(2,6-dimethyl-2-(trimethylsilyloxy)-3,5-heptadionato) copper(II) complex.

(2-3) Preparation of Cu(sopd)$_2$ at Room Temperature in Dimethoxyethane Solvent The preparation in dimethoxyethane solvent is described below.

In 50 mL-volume flask were placed 1.10 g (11.3 mmol) of copper hydroxide, 5.00 g (20.5 mmol) of 2,6-dimethyl-2-(trimethylsilyloxy)-3,5-heptadione, and 15 mL of dimethoxyethane. The resulting mixture was stirred for 2 hours at room temperature in the absence of a dehydrating agent. The resulting dark blue solution was filtered, and the dimethoxyethane solvent was distilled to leave a viscous dark green solution. The solution was distilled at 179° C./0.5 Torr to give 4.57 g (8.30 mmol, yield 81%) of the desired copper complex, namely, bis(2,6-dimethyl-2-(trimethylsilyloxy)-3,5-heptadionato) copper(II) complex.

The copper complex produced in (2-3) above was identified by IR and elemental analysis.

IR (cm$^{-1}$): 3458(br), 2963, 1568, 1518, 1422, 1251, 1196, 1035, 889, 841 Elemental analysis for $C_{24}H_{46}O_6Si_2Cu$ Found: C, 53.0%; H, 8.39%; Cu, 11.5%. Calculated: C, 52.4%; H, 8.42%; Cu, 11.5%. M.p.: 62° C.

The products of (2-1) and (2—2) showed almost same elemental analysis data.

In the IR spectrum, a peak of 1,606 cm$^{-1}$ assignable to β-diketone disappeared, and a peak of 1,568 cm$^{-1}$ assignable to diketonato was observed. The broad peak observed in the vicinity of 3,400 cm$^{-1}$ is assignable to a water of crystallization coordinated to the copper complex. This broad peak was not observed when the product was examined just after the distillation, namely under good conditions.

(3) Vapor Deposition Test

The copper complex of Cu(sopd)$_2$ [represented by the formula (VIII)] prepared in Example 3 was subjected to vapor deposition test according to CVD process, to examine its film forming property. For comparison, the same vapor deposition test was performed using bis(6-ethyl-2,2-dimethyl-3,5-decandionato) copper complex of the aforementioned formula (II).

The test was performed using the apparatus illustrated in FIG. 1. The copper complex 8 placed in a vaporizer (glass ample) 1 was heated by a heater 2 for vaporization. The vaporized complex came out of the vaporizer together with helium gas. The gas coming out of the vaporizer joined a pre-heated hydrogen gas supplied through the hydrogen gas line, and entered the reactor 3. The center portion of the glass reactor could be heated by the heater 4. The copper complex introduced into the reactor reductively decomposed and produced a metallic copper on a surface of a substrate 7 which was set at the center part and heated to the predetermined temperature in a reducing atmosphere. The gas coming out of the reactor was exhausted to atmospheric air through the trap 5.

The copper film-formation depends on the vapor deposition conditions such as the copper complex vaporization temperature and the substrate temperature.

Table 1 shows the vapor deposition conditions employed in the test and the results of film formation. The substrate is a rectangular substrate of 7 mm×4 mm.

TABLE 1

| Example 3: copper complex - Cu(sopd)$_2$ | |
|---|---|
| Condition of vapor deposition | |
| Vaporization temperature: | 140° C. |
| Substrate: | Ta—N/SiO$_2$/Si |
| Substrate temperature: | 230° C. |
| Vaporization period: | 60 min. |
| Pressure in the reaction system: | atmospheric |
| H$_2$ flow rate: | 36 mL/min. |
| He flow rate: | 5 mL/min. |
| Characteristics of formed film | |
| Film thickness: | 200 nm |
| Specific resistance: | 4.5 μΩ cm |
| Appearance: | Smooth glossy metal surface |
| Comparison Example 1: copper complex - bis(6-ethyl-2,2-dimethyl-3,5-decandionato) copper complex | |
| Condition of vapor deposition | |
| Vaporization temperature: | 140° C. |
| Substrate: | Ta—N/SiO$_2$/Si |
| Substrate temperature: | 250° C. |
| Vaporization period: | 60 min. |
| Pressure in the reaction system: | atmospheric |
| H$_2$ flow rate: | 36 mL/min. |
| He flow rate: | 5 mL/min. |
| Characteristics of formed film | |
| Almost no film is produced. | |

The above-mentioned results indicate that the Cu(sopd)$_2$ of the invention shows an excellent film-forming property, as compared with the previously known copper complex.

INDUSTRIAL UTILITY

The copper complex of the invention is a divalent copper complex which is thermally stable, as compared with the thermally unstable monovalent copper complex, and is resistant to thermal decomposition in the vaporizer. Accordingly, it is advantageously employable for industrially preparing a copper-containing film by chemical vapor deposition. Further, the copper complex of the invention can produce a film at a rate greater than that shown by the previously known divalent copper complex. This means that the copper complex of the invention is practically advantageous, and that the copper complex of the invention is favorably employable for the preparation of a copper film widely greatly utilized as the circuit material of semiconductors.

What is claimed is:

1. A divalent copper complex having β-diketonato ligands containing a silyl ether linkage.

2. The copper complex of claim 1, wherein the β-diketonato ligands containing a silyl ether linkage is represented by the formula (I)':

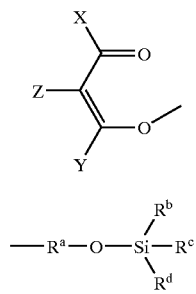

(I)'

(I—I)

in which Z is a hydrogen atom or an alkyl group having 1–4 carbon atoms; X is a group represented by the formula (I—I), in which $R^a$ is a linear or branched alkylene group having 1–5 carbon atoms, and each of $R^b$, $R^c$ and $R^d$ independently is a linear or branched alkyl group having 1–5 carbon atoms; and Y is a linear or branched alkyl group having 1–8 carbon atoms or a group represented by the formula (I—I), in which $R^a$ is a linear or branched alkylene group having 1–5 carbon atoms, and each of $R^b$, $R^c$ and $R^d$ independently is a linear or branched alkyl group having 1–5 carbon atoms.

3. The copper complex of claim 1, which is represented by the formula (I):

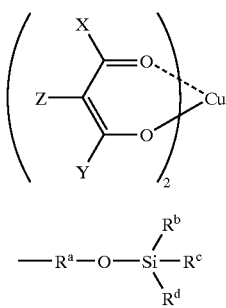

(I)

(I—I)

in which Z is a hydrogen atom or an alkyl group having 1–4 carbon atoms; X is a group represented by the formula (I—I), in which $R^a$ is a linear or branched alkylene group having 1–5 carbon atoms, and each of $R^b$, $R^c$ and $R^d$ independently is a linear or branched alkyl group having 1–5 carbon atoms; and Y is a linear or branched alkyl group having 1–8 carbon atoms or a group represented by the formula (I—I), in which $R^a$ is a linear or branched alkylene group having 1–5 carbon atoms, and each of $R^b$, $R^c$ and $R^d$ independently is a linear or branched alkyl group having 1–5 carbon atoms.

4. The copper complex of claim 2, wherein Y is the same as X.

5. The copper complex of claim 3, wherein Y is the same as X.

6. The copper complex of claim 2, wherein Y is a linear or branched alkyl group having 1–8 carbon atoms.

7. The copper complex of claim 3, wherein Y is a linear or branched alkyl group having 1–8 carbon atoms.

8. The copper complex of claim 2, wherein $R^a$ is an alkylene group having 1–3 carbon atoms which can have one or more alkyl substituent.

9. The copper complex of claim 3, wherein $R^a$ is an alkylene group having 1–3 carbon atoms which can have one or more alkyl substituent.

10. The copper complex of claim 2, wherein Z is a hydrogen atom, and each of $R^b$, $R^c$ and $R^d$ is methyl.

11. The copper complex of claim 3, wherein Z is a hydrogen atom, and each of $R^b$, $R^c$ and $R^d$ is methyl.

12. A method of forming a copper-containing film by chemical vapor deposition using a copper complex of claim 1 as a copper source.

13. A method of forming a copper-containing film by chemical vapor deposition using a copper complex of claim 2 as a copper source.

14. A method of forming a copper-containing film by chemical vapor deposition using a copper complex of claim 3 as a copper source.

\* \* \* \* \*